United States Patent [19]

Hitzel et al.

[11] 4,181,658

[45] Jan. 1, 1980

[54] CERTAIN NICOTINAMIDO-N-BENZOIC ACID DERIVATIVES

[75] Inventors: Volker Hitzel, Hofheim am Taunus; Rudi Weyer, Kelkheim; Karl Geisen, Frankfurt am Main; Werner Pfaff, Hofheim am Taunus, all of Fed. Rep. of Germany

[73] Assignee: Hoechst Aktiengesellschaft, Frankfurt am Main, Fed. Rep. of Germany

[21] Appl. No.: 878,602

[22] Filed: Feb. 16, 1978

[30] Foreign Application Priority Data

Feb. 18, 1977 [DE] Fed. Rep. of Germany ....... 2706977

[51] Int. Cl.² .................. C07D 213/56; A61K 31/44
[52] U.S. Cl. ..................................... 424/266; 546/292
[58] Field of Search ............... 260/295.5 A; 424/266; 546/292

[56] References Cited

U.S. PATENT DOCUMENTS

| | | | |
|---|---|---|---|
| 3,879,403 | 4/1975 | Kuhla et al. | 546/292 |
| 4,001,259 | 1/1977 | Meyer et al. | 546/292 |

*Primary Examiner*—Alan L. Rotman
*Attorney, Agent, or Firm*—Curtis, Morris & Safford

[57] ABSTRACT

Benzoic acid derivatives of the formula

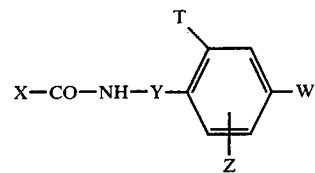

wherein T is hydrogen or halogen, W is a carboxyl group, an ester or salt thereof; X is

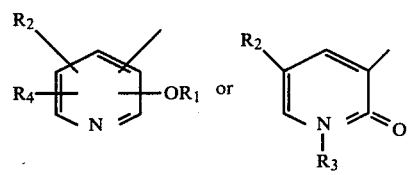

wherein $R_1$ is alkyl having from 2 to 8 carbon atoms, aralkyl or phenyl, cycloalkyl, cycloalkylalkyl or alkylcycloalkyl; $R_2$ is hydrogen or halogen, $R_3$ is alkyl having from 5 to 8 carbon atoms, aralkyl or phenyl, or cycloalkyl having from 5 to 8 carbon atoms; $R_4$ is hydrogen or alkyl; Y is a single chemical bond or a hydrocarbon chain having from 1 to 3 carbon atoms; and Z is hydrogen, halogen, alkyl, alkoxy, alkoxyalkoxy or alkenyloxy, have a blood sugar lowering effect and can be used for the treatment of Diabetes mellitus.

5 Claims, No Drawings

CERTAIN NICOTINAMIDO-N-BENZOIC ACID DERIVATIVES

The present invention provides compounds of the formula

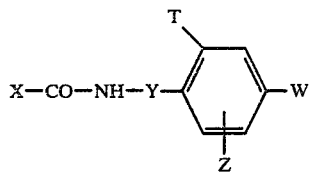

wherein
T is preferably hydrogen or halogen, preferably chlorine or bromine,
W is a carboxyl group, an ester or salt thereof;
X is

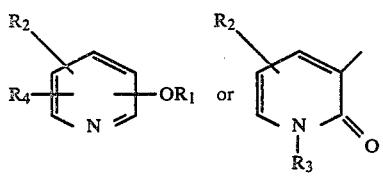

wherein $R_1$ is alkyl having from 2 to 8 carbon atoms, aralkyl or phenyl which may be substituted by alkyl or halogen; cycloalkyl, cycloalkylalkyl, or alkylcycloalkyl, having from 5 to 8 carbon atoms in the ring and up to 3 carbon atoms in the alkyl moieties; $R_2$ is hydrogen or halogen, preferably chlorine or bromine; $R_3$ is alkyl having from 5 to 8 carbon atoms, aralkyl or phenyl, optionally substituted by alkyl or halogen; or cycloalkyl having from 5 to 8 carbon atoms; and $R_4$ is hydrogen and less preferably alkyl especially methyl;
Y is a single chemical bond or a hydrocarbon chain having from 1 to 3 carbon atoms;
Z is hydrogen, halogen, alkyl, alkoxy, alkoxyalkoxy or alkenyloxy.

By alkyl or alkenyl and the alkyl moieties in alkoxy, alkenyloxy, alkoxyalkoxy and alkylamino in accordance with the above definition, there are to be understood linear or branched hydrocarbon radicals having not too great a number of carbon atoms. It has been observed that those compounds the alkyl, alkoxy, alkoxyalkoxy or alkenoxy groups of which have up to 6 carbon atoms are the most efficient ones.

By halogen according to the above definition, there is to be understood above all chlorine and bromine. The corresponding iodine compounds, although quite active too, are less recommended.

For Y preferred chain links are hydrocarbon bridges having 2 carbon atoms which for their part may be substituted also by alkyl groups. The —$CH_2$—$CH_2$ or —$CH(CH_3)$—$CH_2$ group is especially recommended. Other linear or branched hydrocarbon bridges having up to 3 carbon atoms are less preferred.

The present invention provides furthermore a process for the manufacture of the cited compounds, which comprises (a) reacting an amino compound of the formula

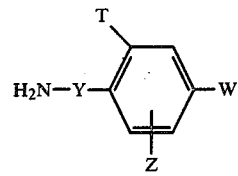

or the formyl compound thereof with a reactive derivative of an acid of the formula XCOOH and optionally splitting off the formyl radical;

(b) converting to a carboxyl group the radical V of a compound of the formula

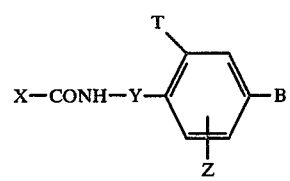

wherein V is a group convertible to a carboxyl group;

(c) alkylating the hydroxy group and a hydroxy group of the radical X, if any, of a compound of the formula

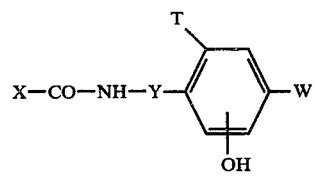

or (d) replacing the halogen atom of a compound of the formula

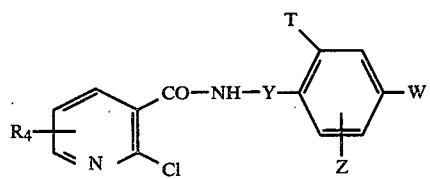

by the radical $OR_1$, and optionally introducing subsequently the radical $R_2$, and optionally converting the compound obtained to a free benzoic acid or an ester or salt thereof.

The amino compounds serving as starting substances according to the operation mode (a) are known and may be prepared without difficulty according to processes known for analogous compounds. These amino compounds are reacted, preferably in the presence of bases, with reactive derivatives of the X—COOH acid, for example its halides, anhydrides, mixed anhydrides, azides or esters.

The starting substances of the operation mode (b) are obtained by acylating an amine of the formula

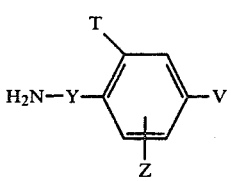

with the radical X'CO—, or, for example, by acylating a compound of the formula

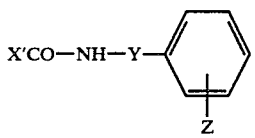

and the starting substances so obtained may be converted to the compounds of the invention by suitable reactions depending on the nature of the group V. In the case where the substituent V is an amide, hydrazide, nitrile, acid halide or ketoacid, hydrolysis is for example a suitable reaction. Oxidation is recommended when V is an alcohol, aldehyde or acyl group. In the case where V is halogen, it may be converted to a carboxyl group by means of a Grignard reaction.

Etherification of the hydroxyl groups according to operation mode (c) is carried out according to known methods, for example by reaction with dialkyl sulfate or alkyl or aralkyl halides.

The reaction of operation mode (d) is carried out with the use of the corresponding alcoholate, if necessary under elevated pressure or temperature.

The compounds of the invention have a blood sugar-lowering effect which may be established by administering the compounds per se, their salts or esters to normally fed rabbits at a dosage rate of from 10 to 400 mg, preferably 100 mg/kg, and by determining the blood sugar concentration for a prolonged period according to the known method of Hagedorn-Jensen, or by means of the autoanalyzer.

The compounds of the invention are preferably used for the manufacture of orally administrable preparations having a blood sugar-lowering action for the treatment of Diabetes mellitus, and they may be applied per se or in the form of their salts or esters or in the presence of substances serving for salt formation, for example alkaline agents such as alkali metal or alkaline earth metal hydroxides, carbonates or bicarbonates.

Suitable medicaments are preferably tablets which, in addition to the compounds of the invention, contain the usual carriers and auxiliaries such as talcum, starch, lactose, tragacanth or magnesium stearate.

A medicament containing the compounds of the invention as active ingredient, for example a tablet or a powder, with or without additives, is advantageously given a suitable dosage form; the individual dose should be adapted to the activity of the compound of the invention and the desired effect. Advantageously, the dose per unit is from about 0.1 to 2 g, preferably 0.5 to 1 g. Doses below or above these ranges may be used. If desired, they may be divided or multiplied before administration.

The benzoic acid derivatives of the invention may be used for the treatment of Diabetes mellitus per se or combined with other antidiabetic agents, that is, not only blood sugar-lowering sulfonyl ureas, but also compounds of different chemical structure, for example biguanides, especially phenylethyl-biguanide or dimethyl-biguanide.

The following examples show some of the numerous variations of the processes for the synthesis of the compounds of the invention, without limiting the scope of the invention.

EXAMPLE 1

4-(2-<2-Butoxy-nicotinamido>-ethyl)-benzoic acid 6.5 g of 2-butoxy-nicotinic acid (melting point=m.p. 54°–56° C., from acetic acid ethyl ester) are dissolved in 150 ml of tetrahydrofuran. After addition of 14.5 ml of triethylamine, the batch is cooled to 0° C., and 3.2 ml of chloroformic acid methyl ester are added dropwise. Agitation is continued for one hour at 0° C., 7.6 g of 4-(2-aminoethyl)-benzoic acid ethyl ester-hydrochloride are added, agitation is continued for a further hour at 0° C., and subsequently for 4 hours at room temperature. The batch is evaporated and the residue is combined with acetic acid ethyl ester. After washing with water, sodium bicarbonate solution, dilute hydrochloric acid and water, the acetic acid ethyl ester solution is dried and evaporated under reduced pressure. The 4-(2-<2-butoxy-nicotin-amido>-ethyl)-benzoic acid ethyl ester so obtained is refluxed for 3 hours in 25 ml of 2 N sodium hydroxide solution and 50 ml of ethanol. After having distilled off the solvent, the product is dissolved in water and acidified with dilute acetic acid, suction-filtered and recrystallized from acetic ester. The 4-(2-<2-butoxy-nicotin-amido>-ethyl)-benzoic acid has a melting point of 147°–149° C.

In analogous manner, there are obtained:
from 2-cyclohexyloxy-nicotinic acid (m.p. 57°–58° C., from ethanol) the 4-(2-<2-cyclohexyloxy-nicotinamido>-ethyl)-benzoic acid m.p. 212°–213° C. (from methanol/dioxan)
from 2-butoxy-5-chloro-nicotinic acid (m.p. 99°–101° C., from acetic acid ethyl ester)
the 4-(2-<2-butoxy-5-chloro-nicotinamido>-ethyl)-benzoic acid, m.p. 164°–166° C. (from methanol/acetic acid ethyl ester)
from 2-phenoxy-nicotinic acid (m.p. 181°–182° C., from acetic acid ethyl ester)
the 4-(2-<2-phenoxy-nicotinamido>-ethyl)-benzoic acid, m.p. 162°–163° C. (from methanol)
from 2-ethoxy-nicotinic acid (m.p. 89°–91° C., from ethanol)
the 4-(2-<2-ethoxy-nicotinamido>-ethyl)-benzoic acid, m.p. 138°–140° C. (from ethanol)
from 2-ethoxy-5-chloro-nicotinic acid (m.p. 115°–117° C., from ethanol)
the 4-(2-<2-ethoxy-5-chloro-nicotinamido>-ethyl)-benzoic acid, m.p. 150°–151° C. (from methanol)
from 2-propoxy-nicotinic acid (m.p. 48°–50° C., from ethanol)
the 4-(2-<2-propoxy-nicotinamido>-ethyl)-benzoic acid, m.p. 157°–158° C. (from methanol)
from 5-chloro-2-propoxy-nicotinic acid (m.p. 102°–103° C., from ethanol)
the 4-(2-<5-chloro-2-propoxy-nicotinamido>-ethyl)-benzoic acid, m.p. 173°–174° C. (from acetic acid ethyl ester)
from 2-pentyloxy-nicotinic acid (m.p. 37°–39° C.)
the 4-(2-<2-pentyloxy-nicotinamido>-ethyl)-benzoic acid m.p. 154°–156° C. (from ethanol)

from 5-chloro-2-pentyloxy-nicotinic acid (m.p. 98°-100° C., from ethanol/H₂O)
the 4-(2-<5-chloro-2-pentyloxy-nicotinamido>-ethyl)-benzoic acid, m.p. 125°-127° C. (from ethanol)
from 2-octyloxy-nicotinic acid (m.p. 53°-54° C.)
the 4-(2-<2-octyloxy-nicotinamido>-ethyl)-benzoic acid, m.p. 104°-106° C. (from ethanol)
from 5-chloro-2-octyloxy-nicotinic acid (m.p. 98°-100° C., from ethanol)
the 4-(2-<5-chloro-2-octyloxy-nicotinamido>-ethyl)-benzoic acid, m.p. 115°-117° C. (from ethanol)
from 5-chloro-2-cyclohexyloxy-nicotinic acid (m.p. 65°-67° C., from acetic acid ethyl ester)
the 4-(2-<5-chloro-2-cyclohexyloxy-nicotinamido>-ethyl)-benzoic acid, m.p. 165°-167° C. (from ethanol)
from 2-benzyloxy-nicotinic acid (m.p. 57°-58° C., from ethanol)
the 4-(2-<2-benzyloxy-nicotinamido>-ethyl)-benzoic acid, m.p. 184°-185° C. (from methanol)

EXAMPLE 2

4-(2-<1-Benzyl-1,2-dihydro-2-oxo-nicotinamido>-ethyl)-benzoic acid 20 ml of acetone are added to 16 ml of an about 1 molar solution of 3-(2-aminoethyl)-benzoic acid containing the corresponding amount of sodium acetate, and 3.7 g of 1-benzyl-1,2-dihydro-2-oxo-nicotinic acid chloride (prepared from 1-benzyl-1,2-dihydro-2-oxo-nicotinic acid and thionyl chloride) are added with agitation and cooling. Agitation is then continued for 1 hour at room temperature, the acetone is removed under reduced pressure, and dilute hydrochloric acid is added to the residue. The precipitated product is suction-filtered, reprecipitated from dilute ammonia, and recrystallized from dilute methanol. The 4-(2-<1-benzyl-1,2-dihydro-2-oxo-nicotinamido>-ethyl)-benzoic acid so obtained has a melting point of 150°-152° C. and of 171°-173° C.

In analogous manner, there are obtained:
from 1-cyclohexyl-1,2-dihydro-2-oxo-nicotinic acid chloride the 4-(2-<1-cyclohexyl-1,2-dihydro-2-oxo-nicotinamido>-ethyl)-benzoic acid, m.p. 176° C. (from ethanol)
from 1-(4-methylcyclohexyl)-1,2-dihydro-2-oxo-nicotinic acid chloride
the 4-(2-<1-(4-methylcyclohexyl)-1,2-dihydro-2-oxo-nicotinamido>-ethyl)-benzoic acid, m.p. 202° C. (from ethanol)

EXAMPLE 3

4-(2-<2-Ethoxy-nicotinamido>-ethyl)-benzoic acid 1.52 g of 4-(2-<2-chloro-nicotinamido>-ethyl)-benzoic acid having a melting point of 205°-206° C. (from acetic ester) (prepared from the mixed anhydride of the 2-chloro-nicotinic acid and 4-(2-aminoethyl)-benzoic acid ethyl ester hydrochloride with subsequent saponification) are dissolved in a solution of 0.23 g of sodium in 50 ml of ethanol. The batch is refluxed for 2 hours while stirring, concentrated under reduced pressure, dissolved in water and acidified with dilute acetic acid. By means of extraction (twice), the product is dissolved in chloroform, and the chloroform phase is dried over sodium sulfate, and concentrated. The solid residue is recrystallized from ethanol. The 4-(2-<2-ethoxy-nicotinamido>-ethyl)-benzoic acid so obtained has a melting point of 138°-140° C. The mixed melting point with the acid obtained according to Example 1 shows no depression.

EXAMPLE 4

4-(2-<2-Ethoxy-5-chloro-nicotinamido>-ethyl)-benzoic acid 3.14 g of 4-(2-<2-ethoxy-nicotinamido>-ethyl)-benzoic acid are suspended in 200 ml of water and heated in an oil bath having a temperature of 60°-70° C. For 3 hours, gaseous chlorine is introduced with agitation into the suspension. After complete reaction (stated by thin-layer chromatography), the batch is allowed to cool, the precipitate is suction-filtered and recrystallized from methanol. The 4-(2-<2-ethoxy-5-chloro-nicotinamido>-ethyl)-benzoic acid so obtained has a melting point of 150°-151° C. and shows no depression in the mixed melting point with the substance obtained according to Example 1.

EXAMPLE 5

4-(2-<5-chloro-hexahydrobenzyloxy-nicotinamido>-ethyl)-benzoic acid 1 g of triethylamine is added to 2.7 g of 5-chloro-2-hexahydrobenzyloxy-nicotinic acid (melting point 150° to 151° C., prepared from 2-chloronicotinic acid by reacting same with hexahydrobenzyl alcohol-sodium with subsequent chlorination with chlorine) in 100 ml of tetrahydrofuran and, after cooling to 0° C., 0.95 g of chloroformic acid methyl ester is added. Stirring of the mixture is continued for 15 minutes at 0° C. and the mixture is added to 10 ml of an about 1 molar solution of 4-(2-aminoethyl)-benzoic acid sodium additionally containing 0.01 mol of sodium acetate, and stirring is continued for 3 hours at room temperature. The major proportion of the solvent is distilled off under reduced pressure and the residue is acidified. The 4-(2-<5-chloro-2-hexahydrobenzyloxy-nicotinamido>-ethyl)-benzoic acid obtained is reprecipitated from ammonia and recrystallized from dilute ethanol. Melting point 177°-178° C.

In analogous manner there are obtained:
from 5-chloro-2-cyclopentyloxy-nicotinic acid (melting point 57°-59° C.)
the 4-(2-<5-chloro-2-cyclopentyloxy-nicotinamido>-ethyl)-benzoic acid melting at 191°-193° C. (from dilute methanol)
from 5-chloro-2-(4-methylcyclohexyloxy)-nicotinic acid (melting point 93°-95° C.)
the 4-(2-<5-chloro-2-(4-methylcyclohexyloxy)-nicotinamido>-ethyl)-benzoic acid melting at 198°-199° C. (from dilute ethanol)

EXAMPLE 6

4-(2-<2-butoxy-6-methyl-nicotinamido>-ethyl)-benzoic acid 2.8 g of triethylamine and 2.6 g of chloroformic acid methyl ester are added while stirring and cooling with ice to 5.3 g of 2-butoxy-6-methyl-nicotinic acid (melting point 52°-54° C.), prepared from 2-chloro-6-methyl-nicotinic acid and sodium butylate) in 75 ml of acetone. Stirring is continued for 15 minutes and, while stirring, the reaction mixture is added to a solution of 0.025 mol of 4-(2-aminoethyl)-benzoic acid-sodium in 25 ml of water containing additionally 0.025 mol of sodium acetate and to which 25 ml of acetone has been added, and stirring of the mixture is continued for a further 2 hours at room temperature. The acetone is distilled off under reduced pressure, the residue acidified with dilute hydrochloric acid, the precipitated product is filtered off with suction, precipitated from dilute ammonia and recrystallized from dilute methanol. The 4-(2-<2-butoxy-6-methyl-nicotinamido>-ethyl)-benzoic acid melts at 128°–130° C.

EXAMPLE 7

4-(2-<2-butoxy-5-chloro-6-methyl-nicotinamido>-ethyl)-benzoic acid 2.8 g of triethylamine and 2.6 g of chloroformic acid methyl ester are added, while stirring and cooling with ice, to 6.1 g of 2-butoxy-5-chloro-6-methyl-nicotinic acid (melting point 95°–97° C., prepared by chlorinating 2-butoxy-6-methyl-nicotinic acid in dilute glacial acetic acid) in 75 ml of acetone. The mixture is stirred for a further 15 minutes and then added, while stirring, to 25 ml of a 1-molar solution of 4-(2-amino-ethyl)-benzoic acid-sodium, additionally containing 0.025 mol of sodium acetate and to which 25 ml of acetone has been added. Stirring of the mixture is continued for 2 hours at room temperature, the acetone is removed under reduced pressure, the remaining aqueous solution is acidified, the precipitated reaction product is filtered off with suction, reprecipitated from ammonia and recrystallized from dilute methanol or ethyl acetate. The 4-(2-<2-butoxy-5-chloro-6-methyl-nicotinamido>-ethyl)-benzoic acid obtained melts at 148°–150° C.

EXAMPLE 8

4-(2-<5-chloro-2-cyclohexyloxy-nicotinamido>-ethyl)-2-methoxy-benzoic acid 6 g of triethylamine and 1.9 g of chloroformic acid methyl ester are added, while stirring and cooling with ice, to 5 g of 5-chloro-2-cyclohexyloxy-nicotinic acid in 150 ml of tetrahydrofuran. Stirring is continued for 30 minutes at 0° C. and, while stirring, 4.6 g of 4-(2-aminoethyl)-2-methoxybenzoic acid are added in the form of its hydrochloride. The mixture is further stirred for 4 hours at room temperature, the solvent removed under reduced pressure, the residue reprecipitated from ammonia and recrystallized from ethanol or ethyl acetate.

The 4-(2-<5-chloro-2-cyclohexyloxy-nicotinamido>-ethyl)-2-methoxy-benzoic acid obtained melts at 170°–172° C.

What is claimed is:

1. A compound of the formula

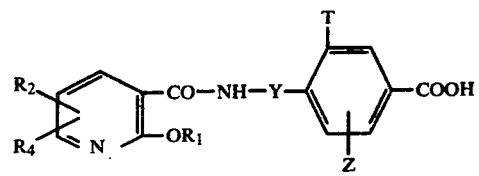

in which $R_1$ is alkyl of 2 to 8 carbon atoms; phenalkyl or phenyl which may be substituted by alkyl or halogen; or cycloalkyl, cycloalkylalkyl or alkylcycloalkyl having from 5 to 8 carbon atoms in the ring and up to 3 carbon atoms in the alkyl moiety;

$R_2$ and T are hydrogen or halogen;

$R_4$ is hydrogen or methyl;

Y is a single chemical bond or a divalent hydrocarbon of 1 to 3 carbon atoms; and Z is hydrogen, halogen or methoxy.

2. A compound as defined in claim 1 in which
$R_2$ is hydrogen or chlorine,
$R_4$ is hydrogen or methyl,
T is hydrogen,
Z is hydrogen or methoxy,
Y is ethylene, and
$R_1$ is alkyl of 2 to 8 carbon atoms, benzyl, phenyl, cyclohexyl, cycloheptyl, cyclohexylmethyl or methylcyclohexyl.

3. 4-(2-<5-chloro-2-cyclohexyloxy-nicotinamido>-ethyl)-benzoic acid.

4. A pharmaceutical preparation for the treatment of Diabetes mellitus which comprises a hypoglycemically effective amount of a compound as defined in claim 1 and a carrier therefor.

5. Treatment of Diabetes mellitus which comprises administering to a diabetic patient a hypoglycemically effective amount of a compound as defined in claim 1.

* * * * *